United States Patent [19]
Hannun et al.

[11] Patent Number: 5,830,916
[45] Date of Patent: Nov. 3, 1998

[54] INHIBITOR OF CERAMIDASE

[75] Inventors: Yusuf A. Hannun, Chapel Hill; Alicja Bielawska, Apex; Charles McKay, Durham, all of N.C.

[73] Assignee: Duke University, Durham, N.C.

[21] Appl. No.: 652,238

[22] Filed: May 23, 1996

[51] Int. Cl.$^6$ ...................................................... A61K 31/16
[52] U.S. Cl. ........................................... 514/625; 514/629
[58] Field of Search ...................... 514/625, 629

[56] References Cited

U.S. PATENT DOCUMENTS

5,369,030  11/1994  Hannun et al. ...................... 435/240.2

*Primary Examiner*—Richard L. Raymond
*Attorney, Agent, or Firm*—Nixon & Vanderhye P.C.

[57] ABSTRACT

The present invention relates, in general, to the bioeffector molecule ceramide and, in particular, to methods of effecting intracellular accumulation of ceramide. The invention further relates to methods of selecting compounds that inhibit alkaline ceramidase and that can be used to treat diseases/disorders associated with cell hyperplasia or dedifferentiation.

6 Claims, 8 Drawing Sheets

(IS, 2R) D-e-MAPP (IR,2S) L-e-MAPP (2S, 3R, 4E) D-e-Ceramide

L-e-MAPP

D-e-Ceramide

INHIBITOR OF CERAMIDASE

This invention was made with Government support under Grant Nos. GM 43825 and DK 45067 awarded by the National Institutes of Health. The Government has certain rights in this invention.

TECHNICAL FIELD

The present invention relates, in general, to the bioeffector molecule ceramide and, in particular, to methods of effecting intracellular accumulation of ceramide. The invention further relates to methods of selecting compounds that inhibit alkaline ceramidase and that can be used to treat diseases/disorders associated with cell hyperplasia or dedifferentiation.

BACKGROUND

Ceramide is an important bioeffector lipid molecule (Hannun, J. Biol. Chem. 269:3125 (1994), Merrill, Jr., Nutr. Rev. 50:78 (1992), Kolesnick and Fuks, J. Exp. Med. 181:1949 (1995), Chao, Mol. Cell. Neurosci. 6:91 (1995), Liscovitch, Trends Biochem. Sci. 17:393 (1992)). The action of a number of extracellular agents as well as stress stimuli, such as $1\alpha,25$-dihydroxyvitamin $D_3$, tumor necrosis factor $\alpha$, interleukin-$1\beta$, neurotrophins, the Fas ligand, dexamethasone, serum withdrawal, chemotherapeutic agents, and $\gamma$-irradiation, causes an elevation in the endogenous levels of ceramide (Hannun, J. Biol. Chem. 269:3125 (1994), Hannun and Obeid, Trends Biochem. Sci. 20:73 (1995), Ballou et al, J. Biol. Chem. 267:20044 (1992), Quintans et al, Biochem. Biophys. Res. Commun. 202:710 (1994), Dobrowsky et al, Science 265:1596 (1994), Yanaga and Watson, FEBS Lett. 314:297 (1992), Dressler and Kolesnick, Science 255:1715 (1992)). A role for endogenous ceramide in mediating, at least in part, the actions of these stimuli on cell differentiation, apoptosis, and growth suppression is supported by the ability of exogenous analogs of ceramide to induce these biologic responses in the respective cell types (Hannun, J. Biol. Chem. 269:3125 (1994), Okazaki et al, J. Biol. Chem. 265:15823 (1990), Bielawska et al, FEBS Lett. 307:211 (1992), Obeid et al, Science 259:1769 (1993), Lauledrkind et al, J. Exp. Med. 182:599 (1995), Goldkorn et al, J. Biol. Chem. 266:16092 (1991)).

Additional evidence for a physiologic function of endogenous ceramide has come from studies examining the specificity of action of ceramide analogs. Thus, it has been shown with $C_2$-ceramide (D-erythro-N-acetylsphingosine) that this molecule demonstrates structural and stereospecific cellular activities (Bielawska et al, J. Biol. Chem. 268:26226 (1993), Fishbein et al, J. Biol. Chem. 268:9255 (1993)). The most significant specificity was demonstrated with the lack of activity of $C_2$-dihydroceramide (Bielawska et al, J. Biol. Chem. 268:26226 (1993), Tepper et al, Proc. Natl. Acad. Sci. U.S.A. 92:8443 (1995)), which differs from $C_2$-ceramide by lacking the trans 4–5 double bond in the sphingoid base; otherwise, these two molecules display identical stereochemistry at the two chiral carbons (C-2 and C-3). Moreover, the cellular uptake and metabolism of these two compounds is nearly identical (Bielawska et al, J. Biol. Chem. 268:26226 (1993)), suggesting that the lack of activity of dihydroceramide is due to inability to interact with relevant intracellular targets. Indeed, $C_2$-ceramide but not $C_2$-dihydroceramide is able to activate ceramide-activated protein phosphatase (CAPP) in vitro (Fishbein et al, J. Biol. Chem. 268:9255 (1993), Dobrowsky et al, J. Biol. Chem. 268:15523 (1993)).

In addition, some of the cellular activities of ceramide have been mimicked by metabolic manipulation of endogenous ceramide levels. Thus, the addition of bacterial sphingomyelinase, which cleaves outer leaflet sphingomyelin and causes accumulation of membrane ceramide, has been shown to mimic at least some of the effects of exogenous cell permeable ceramides (Okazaki et al, J. Biol. Chem. 264:19076 (1989), Mathias et al, Science 259:519 (1993)). Moreover, PDMP and related compounds, which inhibit cerbroside synthase (Abe et al, J. Biochem. (Tokyo) 111:191 (1992)) and also cause accumulation of ceramide, result in cellular activities shared with ceramide. These experimental approaches have lent further credence to a role for endogenous ceramide in cell regulation. They also point to potential versatility in regulation of ceramide levels. Indeed, ceramide occupies a central position in sphingolipid metabolism. Complex sphingolipids derive from ceramide through various enzymatic reactions that add various head groups to the 1-hydroxyl position (Hannun, J. Biol. Chem. 269:3125 (1994), Wiegandt in Glycolipids (Weigandt, ed) pp. 199–259, Elsevier, New York (1985), Merrill, Jr. and Jones, Biochim. Biophys. Acta 1044:1 (1990), Van Echten and Sandhoff J. Biol. Chem. 268:53412 (1993), Hakomori, Annu. Rev. Biochem. 50:733 (1981)). The breakdown of these sphingolipids through sequential metabolic reactions also results in the formation of ceramide. In turn, ceramide can be degraded further through the action of ceramidases resulting in the formation of sphingosine and free fatty acids (Hannun, J. Biol. Chem. 269:3125 (1994), Spence et al, Biochem. Cell Biol. 64:400 (19867), Slife et al, J. Biol. Chem. 264:10371 (1989)).

Figure 1:
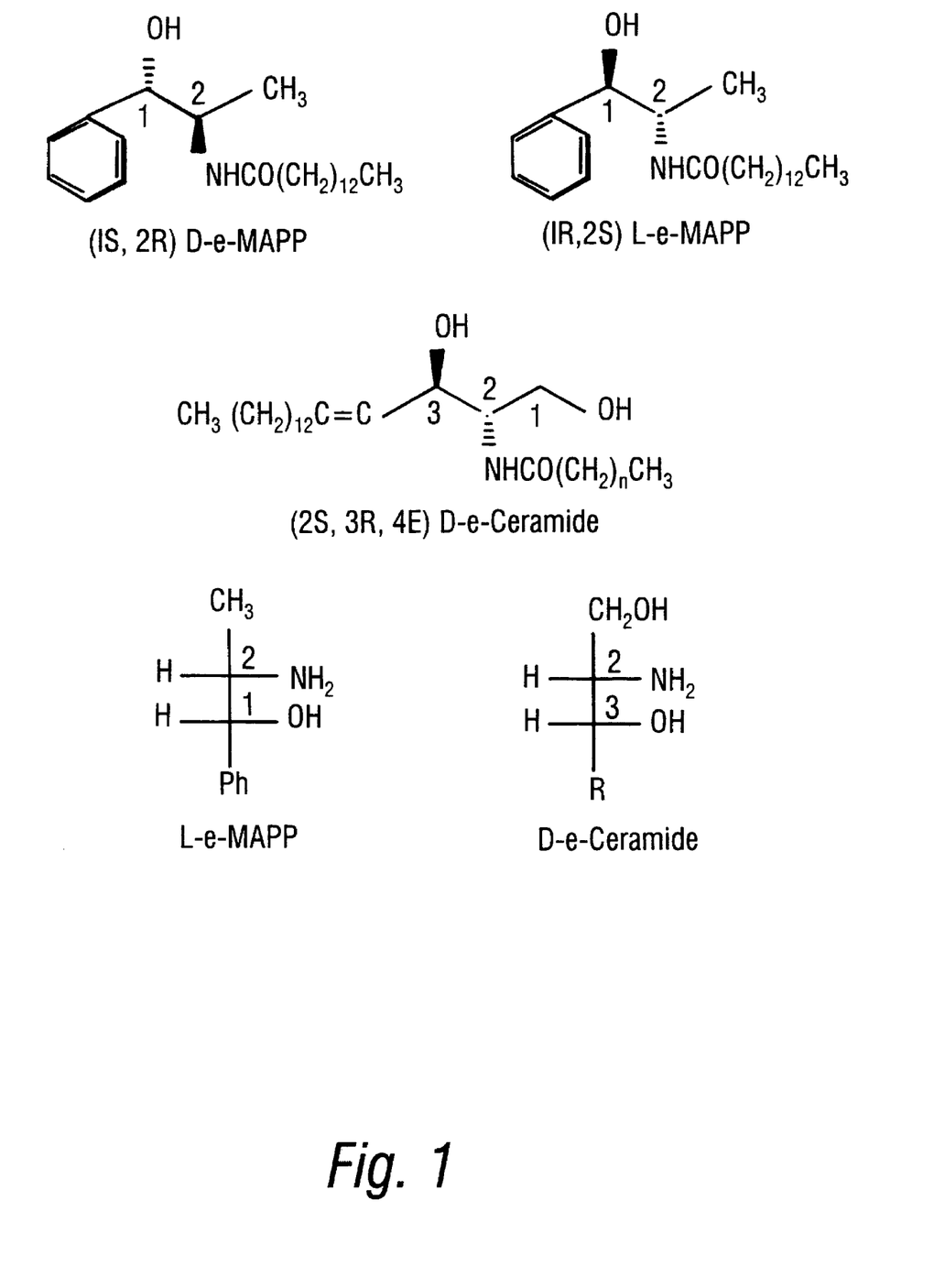
FIG. 1. Structures of D-e-ceramide, D-e-MAPP, and L-e-MAPP. The structure of D-erythro-ceramide is shown vertically-inverted to allow ease of comparison with the configuration of the polar head groups of D- and L-e-MAPP. Also shown are the Fisher projections for D-e-ceramide and L-e-MAPP. In absolute configuration, D-e-ceramide corresponds to L-e-MAPP whereas D-e-MAPP has the enantiomeric configuration.

The activity of a number of synthetic ceramide analogs based on N-acylated phenylaminopropanols has been examined (Bielawska et al, J. Biol. Chem. 267:18493 (1992), U.S. Pat. No. 5,369,030). Two of these analogs, D-erythro-MAPP (D-erythro-2-(N-myristolyamino)-1-phenyl-1-propanol) and L-erythro-MAPP (L-erythro-2-(N-myristolyamino)-1-phenyl-1-propanol), are of particular interest because they demonstrated enantiomeric selectivity of action. Examination of the absolute stereochemistry of these molecules (shown in FIG. 1) reveals that D-erythro-MAPP has an absolute configuration corresponding to L-erythro-ceramide, whereas L-erythro-MAPP has an absolute configuration corresponding to D-erythro-ceramide.

The present invention results, at least in part, from the demonstration that L-e-MAPP is a substrate for alkaline ceramidase whereas D-e-MAPP inhibits this enzyme and results in substantial elevation in intracellular levels of ceramide. This demonstration makes possible methods of selecting compounds that act as specific inhibitors of alkaline ceramidase, which compounds can be used to treat a variety of hyperproliferative diseases/disorders.

SUMMARY OF THE INVENTION

It is a general object of the invention to provide a method of selecting compounds that cause intracellular accumulation of ceramide.

It is a specific object of the invention to provide a method of identifying compounds that can be used to effect the selective inhibition of alkaline ceramidase.

It is a further object of the invention to provide a method of selecting compounds that can be used to treat hyperproliferative diseases/disorders.

The foregoing objects are met by the present invention.

In one embodiment, the present invention relates to a method of increasing intracellular levels of ceramide in a mammal. The method comprises administering to the mammal an agent that inhibits alkaline ceramidase in an amount sufficient to effect the inhibition, and monitoring the intracellular levels of ceramide.

In a further embodiment, the present invention relates to a method of treating a disease or disorder associated with cell hyperplasia. The method comprises administering to a mammal in need of such treatment an agent that inhibits alkaline ceramidase in an amount sufficient to effect the inhibition, and monitoring intracellular levels of ceramide in the mammal.

In yet another embodiment, the present invention relates to a method of testing a compound for its ability to inhibit mammalian alkaline ceramidase. The method comprises
i) contacting the compound with a sample comprising mammalian alkaline ceramidase, in the presence of ceramide, under conditions such that the alkaline ceramidase degrades ceramide to sphingosine in the absence of the compound, and
ii) determining the level of degradation of ceramide resulting from step (i) and comparing that level to a level of degradation obtained in the absence of the compound.

Further objects and advantages of the invention will be clear from the description that follows.

BRIEF DESCRIPTION OF THE DRAWINGS

FIG. 5. Uptake and metabolism of D- and L-MAPP. HL-60 cells were treated with tritium-labeled D- and L-e-MAPP. A, back-extraction of D-e-MAPP taken up by cells. HL-60 cells were incubated with 5 µM tritium-labeled D-e-MAPP, and radioactivity associated with cells was determined before (no wash) or following the indicated number of washes. B, effect of duration of exposure of HL-60 cells to D-e-MAPP on growth suppression. HL-60 cells were treated with 5 µM D-e-MAPP which was back-extracted with 5 washes at the indicated time points. C, total uptake of D-e-MAPP and L-e-MAPP. HL-60 cells were treated with the indicated concentrations of tritium-labeled D- and L-e-MAPP, and total radioactivity associated with the cell pellet was determined. ■, 5 µM D-MAPP; ▨, 30 µM D-MAPP; ▨, 5 µM L-MAPP; ▨, 30 µM L-MAPP; D, TLC separation of intact tritium-labeled D- and L-e-MAPP and their metabolites. Cells were treated with 5 µM D- or L-e-MAPP, and lipids were extracted at the 24-h time point and resolved on TLC. E, time dependence of metabolism of D- and L-e-MAPP. HL-60 cells were treated with 5 µM D- or L-e-MAPP. Intact compounds and their metabolites were resolved by TLC and radioactivity associated with each spot was determined by scintillation counting of the excised spots. Δ, D-MAPP; ●, L-MAPP; ○, L-MAPP (upper spot); ■, myristoyl-CoA.

FIG. 6. Effects of D- and L-e-MAPP on alkaline and acid ceramidase activity in vitro. Ceramidase activity was determined from total homogenates of HL-60 cells. A, pH dependence of ceramidase activity from HL-60 cells. Ceramidase activity using tritium-labeled $C_{16}$-ceramide was measured in vitro using sodium acetate, HEPES, and CHES buffers over a pH range of 4.5 to 9.0. B, substrate preference of ceramidase in vitro. Tritium-labeled $C_{16}$-ceramide, D-e-MAPP, or L-e-MAPP were used as substrates in an in vitro ceramidase assay at 50 µM concentrations. Activity was determined by measuring release of the tritium-labeled acyl chains. C, inhibition of acid ceramidase by D-e-MAPP and N-oleoylethanolamine. Ceramidase activity was evaluated in vitro at pH 4.5 using 50 µM $C_{16}$ ceramide as a substrate in the presence of increasing concentrations of D-e-MAPP or N-oleoylethanolamine. Data are presented as mean activity normalized to control activity in samples treated with vehicle alone. D, inhibition of alkaline ceramidase by D-e-MAPP and N-oleoylethanolamine. Ceramidase activity was evaluated in vitro at pH 9.0 using 50 µM $C_{16}$ ceramide as a substrate in the presence of increasing concentrations of D-e-MAPP (D-MAPP) or N-oleoylethanolamine (NOE). Data are presented as mean activity normalized to control activity in samples treated with vehicle alone.

DETAILED DESCRIPTION OF THE INVENTION

The present invention results, at least in part, from the observation that D-e-MAPP functions as an inhibitor of alkaline ceramidase. The biological consequences of this inhibition mimic those associated with exogenous ceramides. These observations make possible the regulation of endogenous ceramide levels and the identification of compounds that can be used to selectively inhibit alkaline ceramidase activity and thereby inhibit cell growth or induce cell differentiation. It is expected that compounds suitable for use in the invention include, generally, amides of hydrophobic molecules having the stereochemistry of D-e-MAPP, eg, molecules of the formula wherein $R_1$, $R_2$, $R_3$ and $R_4$ are such that of the molecule is hydrophobic and no two of $R_1$, $R_2$, $R_3$ and $R_4$ are hydrogen.

U.S. Pat. No. 5,369,030 relates to the use of N-acyl-phenylaminoalcohol analogs to induce cellular differentiation and to alter cell phenotype. U.S. Pat. No. 5,369,030 further relates to the use of such analogs to treat diseases/disorders characterized by cell hyperproliferation. The compounds disclosed in U.S. Pat. No. 5,369,030 and their methods of use (for example, in treating malignant (eg cancer, leukemia and lymphoma), premalignant (eg myelodysplasia) or benign (eg lymphoma, proliferative, benign tumors and psoriasis) diseases/disorders) are incorporated herein by reference.

One compound disclosed in U.S. Pat. No. 5,369,030, D-e-MAPP, is shown in the Examples that follow to be capable of effecting concentration- and time-dependent suppression of cell growth, accompanied by an arrest in the $G_0/G_1$ phase of the cell cycle. The data presented in the Examples demonstrate that these effects result from the selective inhibition by D-e-MAPP of alkaline ceramidase activity. This demonstration makes it possible to screen compounds for their ability to increase endogenous ceramide levels by selectively inhibiting alkaline ceramidase activity and to distinguish between compounds that increase ceramide levels by inhibiting degradation of ceramide to sphingosine and those that do not result in such inhibition.

In a broad sense, the present invention relates to a method of treating a disease or disorder associated with cell dedifferentiation or hyperproliferation. The method comprises administereing to an individual in need of such treatment an agent that selectively inhibits alkaline ceramidase, in an amount sufficient to effect the inhibition. Suitable agents include N-acyl-phenylaminoalcohols of U.S. Pat. No. 5,369,030, specifically, compounds disclosed therein having an absolute stereochemical configuration opposite that D-erythro-ceramide.

The above-indicated compounds can be prepared as described in U.S. Pat. No. 5,369,030, and formulated into pharmaceutical compositions as described therein. Administration protocols can be used as described in U.S. Pat. No. 5,369,030 to effect the indicated treatments.

Compounds, in addition to those described above, can be selected for their suitability for use in treating diseases and disorders associated with cell hyperplasia or dedifferentiation by screening test compounds for their ability to inhibit alkaline ceramidase. Such screens constitute a further embodiment of the invention. In this embodiment, purified or partially purified preparations of ceramidase (either naturally occurring or recombinantly produced) can be used (examples of suitable preparations are described in the Examples that follow). A reaction mixture comprising the enzyme, ceramide and the test compound can be incubated, for example, at a pH in the range of 6.5° to 10° (preferably about 9.0°), at about 37° C. for about 1 hour. The reaction can be monitored, for example, by determining the extent of ceramide degradation or sphingosine or fatty acid production. In the Examples that follow, ceramide labeled with a detectable label (eg radioactive (eg tritiated) ceramide) is used as substrate and the reaction monitored by separating the labeled products (eg radiolabeled-fatty acid). Various other techniques for monitoring can be used, however, including various other detectable labels (eg fluorescent labels).

In accordance with this screening approach, the ceramidase activity is determined at various concentrations of the test compound. Those compounds that result in about a 50% inhibition of enzyme activity, or greater, at a concentration in the range of 1 nM to 50 $\mu$M are preferred.

In addition to a system of the type described above, the present invention also related to screens wherein a known alkaline ceramidase inhibitor is incubated with a test compound, a ceramidase preparation and ceramide (under conditions, for example, as described above). The ability of the test compound to shift the dose response curve of the known inhibitor to the left is indicative of a compound that inhibits alkaline ceramidase and thus that is useful in treating cell hyperproliferative disorders/diseases. Compounds that enhance alkaline ceramidase inhibitory activity can be further tested for stability, toxicity, etc, using standard protocols.

Compounds selected for their ability to inhibit alkaline ceramidase can be formulated into pharmaceutical compositions and used therapeutically as described above. Subjects susceptible to therapy involving the use of the present compounds can be identified by isolating a biological sample from the subject and determining whether ceramidase present in that sample can be inhibited (for example, under conditions such as those described above) by the selected inhibitor.

It will be appreciated that the preferred subject of the invention is a human, however, veterinary uses are also contemplated.

The demonstration that compounds of the D-e-MAPP-type inhibit alkaline ceramidase makes possible protocols suitable for purifying the enzyme. For example, potent inhibitors can be used to affinity purify ceramidase, for example, from crude cellular preparations using art recognized affinity purification techniques.

Certain aspects of the present invention are described in greater detail in the non-limiting Examples that follow.

EXAMPLES

The following experimental details relate to the Examples that follow.

Proliferation and cell cycle studies. HL-60 human myelocytic leukemia cells (obtained from the American Type Culture Collection) were grown in RPMI 1640 medium containing 10% fetal calf serum at 37° C. in 5% $CO_2$ incubator. For proliferation and cell cycle studies, cells were resuspended at a density of $2\times10^5$ cells/ml in serum-free media containing insulin (5 mg/liter) and transferrin (5 mg/liter) and sodium selenite (5 $\mu$g/liter) for 2–4 h. Cells were then treated with the indicated compounds. Ethanol concentration was always maintained at less than 0.1%. Cell proliferation was determined by counting cells using a hemacytometer, cell viability was evaluated by trypan blue dye exclusion, and cell cycle analysis was determined by propidium iodide flow cytometry as described (Chao et al, J. Biol. Chem. 267:23459 (1992)).

Synthesis and labeling of D-e-MAPP and L-e-MAPP. D- and L-MAPP were prepared by acylation of D- and L-erythro-2-amino-1-phenyl-1-propanol with myristoyl chloride as described (Bielawska et al, J. Biol. Chem. 267:18493 (1992)). 2-(N-[$^3$H]myristolamino)-1-phenyl-1-propanols, D-[$^3$H]MAPP, and L-[$^3$H]MAPP were prepared following the general procedure for MAPP synthesis using [$^3$H]myristic acid converted to [$^3$H]myristoyl chloride or N-succinimidyl-[$^3$H]myristoanate.

Ceramide and diacylglycerol levels. Ceramide and diacylglycerol levels were measured on total liquid extracts using the diacylglycerol kinase assay (Jayadev et al, J. Biol. Chem. 270:2047 (1995)).

Synthesis of 2-(N-[$^3$H-palmitylamino)-sphingosine($^3$H] $C_{16}$-ceramide). Synthesis was performed by acylation of (2S,3R)-sphingosine with [$^3$H]palmitic acid converted to [$^3$H]palmitoyl chloride or N-succinimidyl-[$^3$H]palmitoanate (Jayadev et al, J. Biol. Chem. 270:2047 (1995)). A crude product was purified via the flash chromatography method (EM-Science silica gel; 40–65 µm) using a methylene chloride/methanol system with increasing polarity from 100:0 to 98:4 and were crystallized from ethanol. The purity of the obtained compound was assessed by TLC analysis using Merck pre-coated Silica Gel 60 F-254 plates and methylene chloride/methanol, 93:7, or chloroform/methanol, 4:1, solvent systems to develop plates. TLC spot detection was by iodine vapor and 5% potassium parmanganate in 1N potassium hydroxide. Structure of nonradioactive amides was verified by proton-NMR ($^1$H NMR), mass spectroscopy (MS), and CD spectra. Specific activity of the obtained N-[$^3$H]acyl derivatives was ~3–4×10$^4$ dpm/nmol, and the purity was close to 100%.

Uptake and metabolism studies. HL-60 cells were grown as described and treated with $^3$H-labeled compounds at concentrations ranging from 0 to 10 µM. At the indicated time points, cell pellets were separated from media and $^3$H radioactivity was counted.

Metabolism studies. Lipids from cells treated with $^3$H-labeled compounds were extracted (Bligh & Dyer method), dried, resuspended in chloroform/methnol (10:1, v/v), and subjected to separation by TLC in chloroform/methanol (4:1, v/v). Spots containing radioactive compounds were scraped and radioactivity was measured using a scintillation counter.

Measurement of ceramidase activity in HL-60 cells. Ceramidase activity in HL-60 cells was measured by a modification of the method of Gatt and Yavin (Methods Enzymol. 14:139 (1969)). Cells were disrupted by sonication in 0.25M sucrose, 1 mM EDTA, and centrifuged at 10,000×g for 10 min after which the supernatant was centrifuged at 100, 000×g for 60 min. Ten µl of 1 mM ceramide substrate ([$^3$H]$C_{16}$-ceramide) was mixed with 100 µl of Triton X-100 (0.1%) in chloroform/methanol, 2:1, and 100 µl of 0.2% sodium cholate in chloroform/methanol, 2:1, after which the solvent was evaporated under $N_2$ at 70° C. To this mixture, 30 µl of water was added and the tubes were heated for 5 s in an 80° C. water bath and then put on ice. Fifty µl of the appropriate buffer depending on desired pH was added followed by 20 µl of 50 mM $MgCl_2$ and 100 µl of cell extract. In experiments using inhibitors, the desired inhibitor was added in ethanol either with the substrate or directly to the final solution. The reaction mixture was incubated for 1 h at 37° C. The $^3$H-fatty acid products of ceramidase were separated by the addition of 2 ml of Dole's solution (isopropyl alcohol, heptane, NaOH), 1.2 ml of heptane, and 1 ml of water. After vortexing and centrifugation, the upper phase was discarded and the lower phase was washed twice with heptane and the upper phase discarded each time. Finally, 1 ml of 1N $H_2SO_4$, and 2 ml of heptane were added, and after vortexing and centrifugation the upper phase was transferred for counting by liquid scintillation.

Glucocerebrosidase and glucocerebroside synthase assays. In vitro assays for gluccerebrosidase and for cerebroside synthase were performed as described (Abe et al, J. Biochem. (Tokyo) 11:191 (1992)).

CAPP. The activity of CAPP was determined as described previously (Dobrowsky and Hannun, J. Biol. Chem. 267:5048 (1992)) using myelin basic protein (phosphorylated by protein kinase A) as a substrate.

Example I

Cellular Activition of D- and L-Erythro-MAPP

Figure 2A:
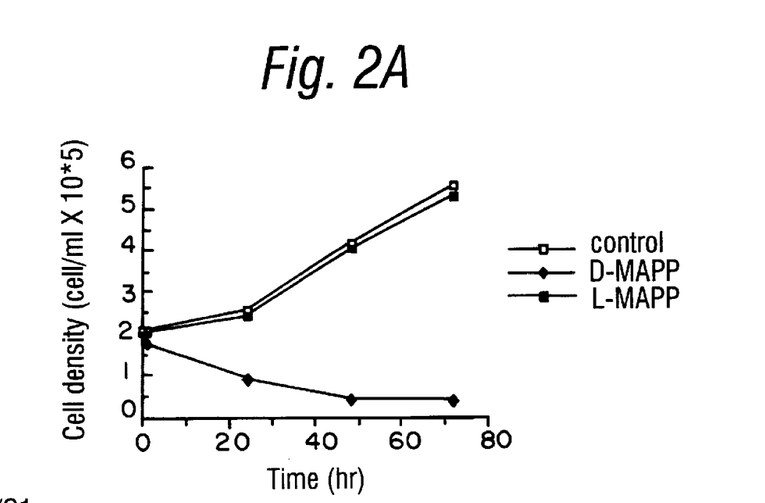
FIG. 2. Effects of D- and L-e-MAPP on cell growth. HL-60 cells were treated with 5 µM of either D-e-MAPP or L-e-MAPP and growth was monitored over the indicated time range (A). The effects of 5 µM D- and L-e-MAPP on cell cycle progression was determined at 48 h (B).

In structure-function analysis of ceramide-mediated growth suppression using amides of phenylaminoalcohols, D- and L-erythro-MAPP were employed. In these studies, HL-60 cells were treated with 5 µM of either D-E-MAPP or L-e-MAPP, and growth was determined at the indicated time points (FIG. 2A). D-erythro-MAPP produced a time dependent suppression of growth that was predominantly characterized by a cytostatic effect on proliferation. On the other hand, L-erythro-MAPP was largely inactive (FIG. 2A).

Figure 2B:
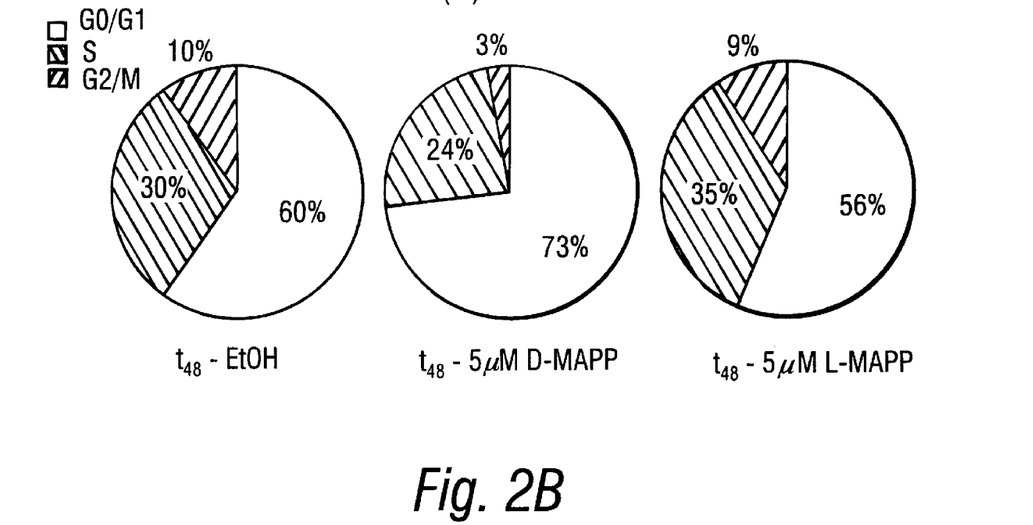

In order to evaluate if D-erythro-MAPP modulated cell cycle progression, HL-60 cells were treated with 5 µM D-e-MAPP, and cell analysis was performed at 48 h using propidium iodide flow cytometry. These studies showed that D-erythro-MAPP produced a significant increase in the population of cells in the $G_0/G_1$ phase of the cell cycle (from 60 to 73%) with a corresponding drop in the population of cells in S (from 30 to 24%) and $G_2/M$ (from 10 to 3%) phases of the cell cycle (FIG. 2B). On the other hand, 5 µM L-e-MAPP was largely without effect (FIG. 2B). These studies show that a predominant effect of D-e-MAPP is the induction of a $G_0/G_1$ arrest in cell cycle progression resulting in growth suppression.

Example II

Effects on CAPP

Figure 3:
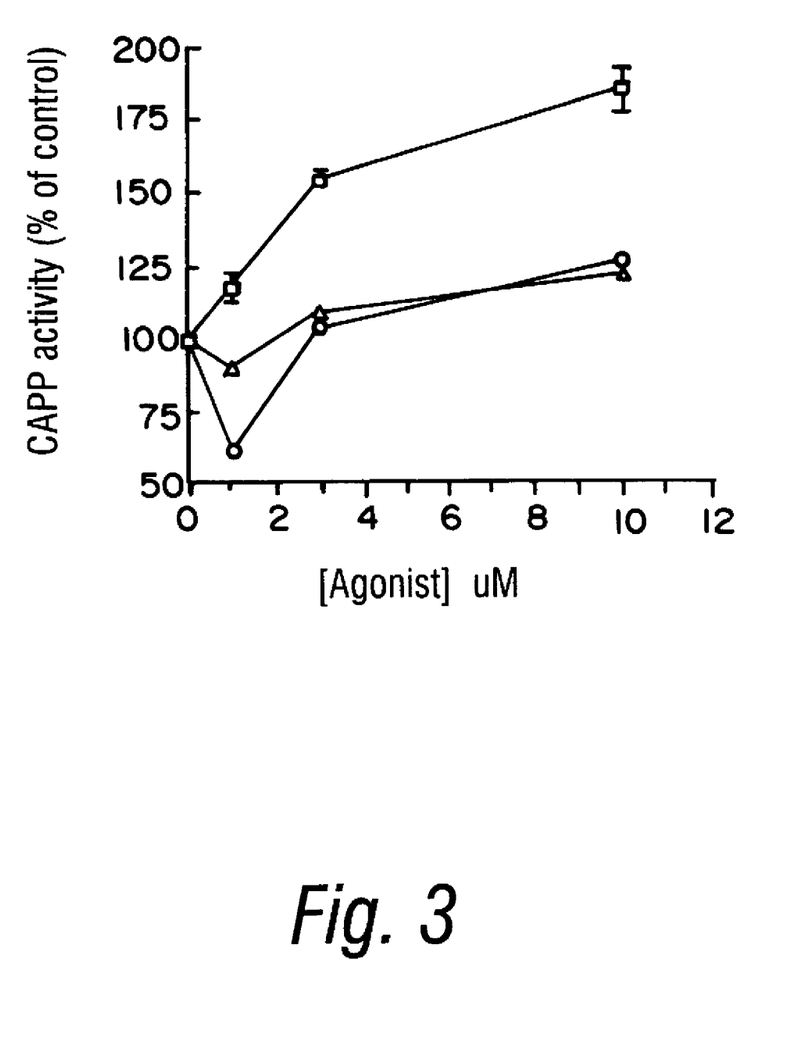
FIG. 3. Effects of D- and L-e-MAPP on CAPP. The serine/threonine phosphatase activity of CAPP was determined using as substrate myelin basic protein phosphorylated by protein kinase A. □, $C_6$-ceramide; ○, D-MAPP; Δ, L-MAPP.

Since D-e-MAPP mimicked the cellular activities of ceramide, it was determined whether D-e-MAPP mimicked the in vitro activity of ceramides. In vitro ceramides of varying N-linked chain lengths activate a serine/threonine protein phosphatase (CAPP), with a specificity matching the specificity of the cellular activities of ceramides (Wolff et al, J. Biol. Chem. 269:19605 (1994)). CAPP appears to belong to the heterotrimeric subfamily of the PP2A family of protein phosphatases (Dobrowsky et al, J. Biol. Chem. 268:15523 (1993)). Addition of $C_6$-ceramide to CAPP in vitro resulted in a concentration-dependent stimulation of activity (FIG. 8). On the other hand, neither D-e-MAPP nor L-e-MAPP activated CAPP in vitro (FIG. 3), raising the possibility that D-E-MAPP may not function as a direct analog of ceramide.

Example III

Effects of D- and L-MAPP on Endogenous Levels of Ceramide

Figure 4A:
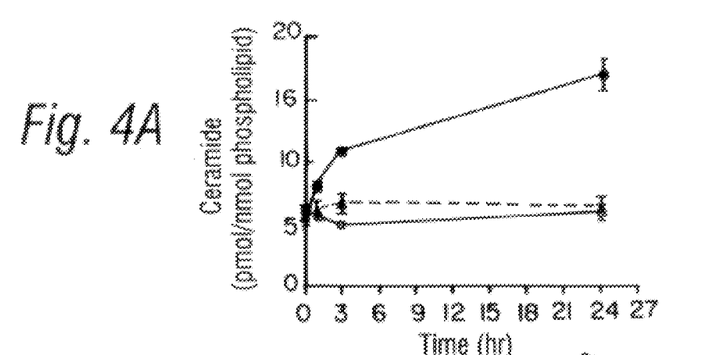
FIG. 4. Effects of D- and L-e-MAPP on endogenous levels of ceramide. HL-60 cells were treated with 5 µM D- or L-e-MAPP, and lipids were extracted for ceramide measurements at the indicated time points. A, the effects of D- and L-e-MAPP on total ceramide levels standardized to total levels of lipid phosphate. □, control; ●, D-MAPP; ▲, L-MAPP. B, TLC separation of diacylglycerol kinase products of synthetic D-erythro-$C_{18}$-ceramide, D-erythro-$C_{18}$-dihydroceramide, and ceramide from bovine brain sphingomyelin. C, relative changes in the levels of ceramide and dihydroceramide following the addition of D-e-MAPP to cells. Ceramide and dihydroceramide were quantitated as the respective phosphates.

Since D-erythro-MAPP, the bioactive enantiomer, corresponds in absolute configuration to L-erythro-ceramide (the unnatural enantiomer of ceramide) (FIG. 1), and since it lacks in vitro activity with CAPP, it was determined whether D-E-MAPP mimicked ceramide biology by modulation endogenous ceramide levels. Therefore, HL-60 cells were treated with 5 µM D-e-MAPP, ethanol vehicle or L-e-MAPP for 0–24 h. At the indicated time points (FIG. 4A), total lipids were extracted and endogenous ceramide levels were measured by the *Escherichia coli* diacylglycerol kinase assay. In control cells, there were no changes in endogenous ceramide levels, and in cells treated with L-e-MAPP there were very modest changes (~20%) in ceramide levels; especially at the early time points (FIG. 4A). However, the addition of D-e-MAPP resulted in a time dependent accumulation of endogenous levels of ceramide reaching approximately 3-fold of baseline by the 24-h time point. These results demonstrate that, as compared to L-e-MAPP, D-e-MAPP selectively regulates endogenous ceramide levels.

Figure 4B:
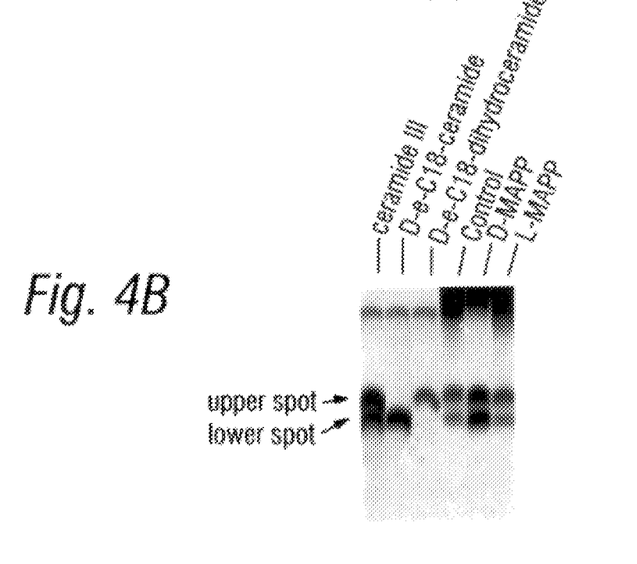
Figure 4C:
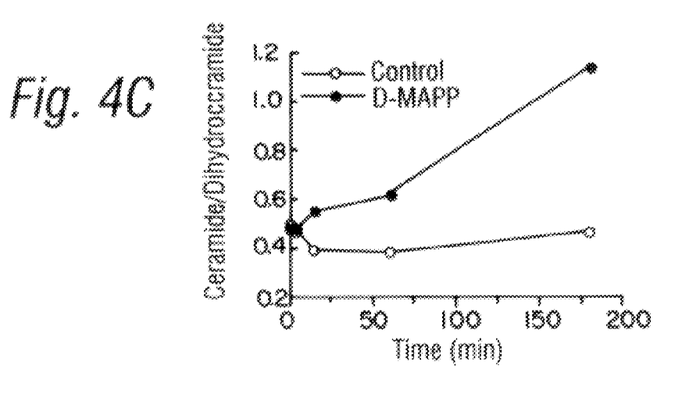

The results from the diacylglycerol kinase assay revealed that D-e-MAPP selectively modulated the levels mostly of one of two major species of ceramide phosphate (the product of ceramide transformation by the diacylglycerol kinase assay) as detected by TLC (FIG. 4B). The upper spot of ceramide phosphate co-migrated with synthetic D-erythro-$C_{18}$ dihydroceramide phosphate whereas the lower spot co-migrated with D-erythro-$C_{18}$ ceramide phosphate. FIG. 4C shows that the addition of D-e-MAPP resulted in selective enhancement in the levels of the lower spot of ceramide phosphate. Based on this co-migration, the results suggest that D-e-MAPP causes a selective increase in ceramide but not dihydroceramide levels. It should be noted, however, that the structure of these species of ceramide phosphate has not been determined conclusively.

Example IV

Uptake and Metabolism of D- and L-MAPP

Figure 5A:
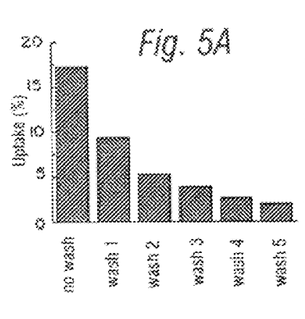
Figure 5B:
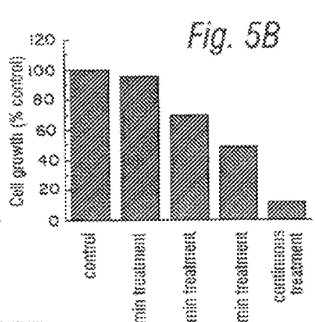

Studies were conducted examining the uptake and metabolism of D- and L-MAPP. In the first set of studies, the effect of duration of exposure of HL-60 cells to D-e-MAPP on the bioactivity of the molecule was determined. D-e-MAPP added to cells could be washed off by repeated sedimentation and washing of cells. Thus, after five cycles of washing, less than 10% of D-MAPP remained associated with the cell pellet compared to unwashed cells (FIG. 5A). The continuous exposure of HL-60 cells to D-MAPP resulted in dramatic growth inhibition (FIG. 5A) as compared to vehicle-treated cells. Exposure of HL-60 cells to D-MAPP for only 15 min did not affect cell growth, whereas exposure for progressively longer intervals resulted in increased growth suppression (FIG. 5B). These results show that the ability of D-e-MAPP to inhibit growth requires prolonged exposure of cells to this compound and suggest that the effects of D-e-MAPP require continuous interactions with intracellular targets (such as ceramide-metabolizing enzymes).

Figure 5C:
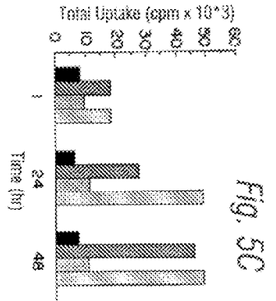
Figure 5D:
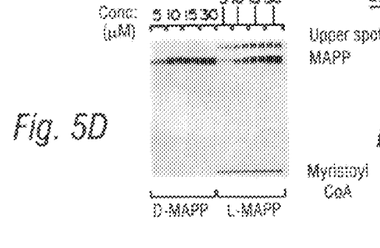
Figure 5E:
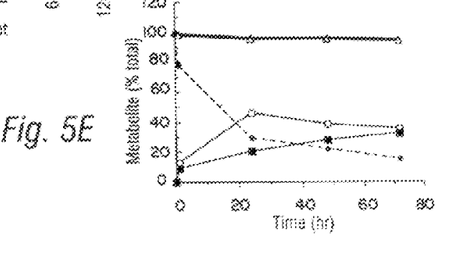

Next, the uptake of tritium-labeled D- and L-e-MAPP was examined. To this end, D- and L-e-MAPP labeled in the N-myristoyl group were synthesized and used for uptake and metabolism studies. The addition of 5 or 30 µM of either D- or L-e-MAPP resulted in a dose- and time-dependent increase in uptake of the molecules (FIG. 5C). At 24 hr, approximately 20% of D-e-MAPP (5 µM) and 26% of L-e-MAPP (5 µM) were taken up by cells.

The partitioning of the label taken up by cells into the lipid organic phase was evaluated next. It was found that the majority of the label in D-e-MAPP or L-e-MAPP remained associated with the organic phase over a 0–72 h duration at concentrations ranging from 5 to 30 µM.

Next, the metabolism of D- and L-e-MAPP was evaluated. To this end, organic lipids were extracted from cells treated with 5 µM D- or L-e-MAPP at the indicated time points (FIG. 5D), and lipids were resolved on TLC. D-e-MAPP showed little metabolism and remained intact throughout the duration of the experiment (FIG. 5, D and E). On the other hand, L-e-MAPP underwent significant metabolism in a time-dependent fashion such that by 24 h, more than 70% of the L-e-MAPP taken up by cells was metabolized (FIG. 5, D and E). Two major breakdown products of L-e-MAPP were resolved by TLC. One metabolite co-migrated with myristoyl-CoA and not with other neutral or polar lipids. The other metabolite (upper spot in FIG. 5D) comigrated with triacylglycerol. These results are of 2-fold significance. First, they suggest that the major reason for the lack of activity of L-e-MAPP may be due to its relatively rapid metabolism. Second, they show that L-e-MAPP is a substrate for endogenous ceramidases that are capable of releasing the N-linked myristate. On the other hand, D-e-MAPP does not appear to be a substrate for this enzyme.

Example V

Effects of D- and L-e-MAPP on Ceramide-Metabolizing Enzymes

Figure 6A:
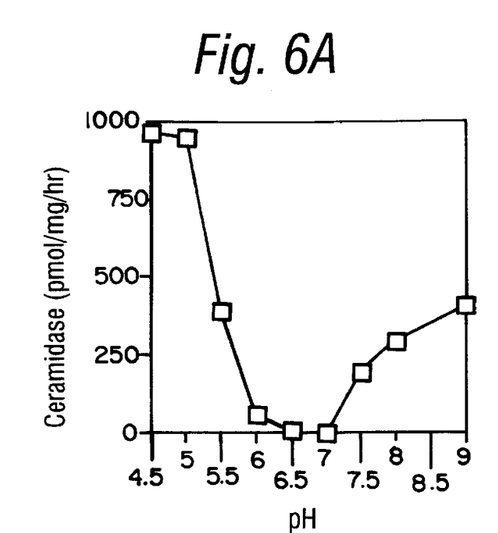
Figure 6B:
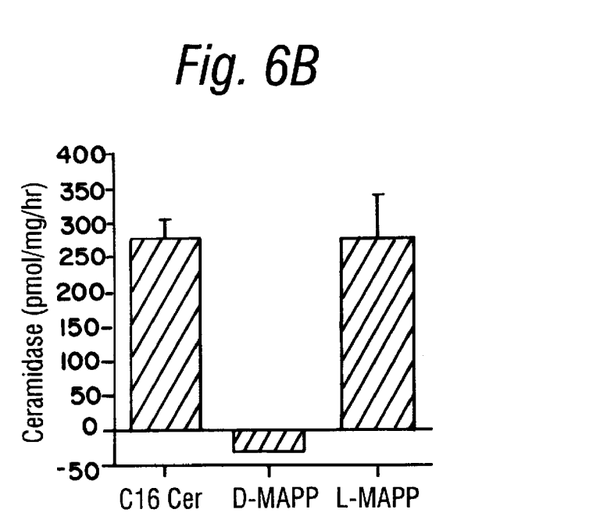

In order to evaluate the interactions of D- and L-e-MAPP with ceramidase, in vitro studies we conducted using cytosolic and membrane fractions from HL-60 cells. Initially, ceramidase activity was examined for pH dependence using tritium-labeled $C_{16}$-ceramide as substrate. Ceramidase activity was found to exist predominantly in the membrane fraction at two separate pH optima of 4.5 and 9.0 (FIG. 6A). The alkaline ceramidase activity was very similar to that described in fibroblasts and cerebellar tissue (Sugita et al, Biochim. Biophys. Acta 398:125 (1975), Wertz and Downing, FEBS Lett. 268:110 (1990)). In initial studies, the ability of this ceramidase to utilize D-e- and L-e-MAPP as substrates was investigated. D-e-MAPP was not substrate for the alkaline ceramidase (FIG. 6B). In contrast, L-e-MAPP was readily hydrolyzed by ceramidase to a level equivalent to that seen with $C_{16}$-ceramide as a substrate (FIG. 6B). These studies corroborate the cellular metabolism studies showing that L-e-MAPP is a substrate for ceramidase in vitro and in cells.

Figure 6C:
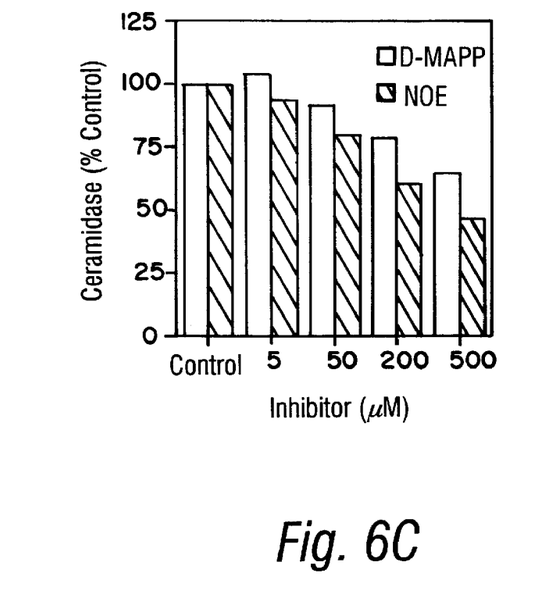
Figure 6D:
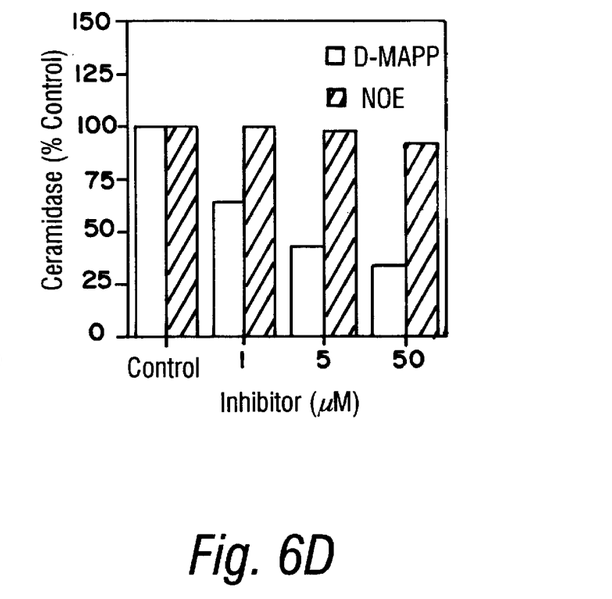

Next, the ability of D- and L-e-MAPP to interfere with hydrolysis of $C_{16}$-ceramide by ceramidase at pH 4.5 and 9.0 was evaluated. Inhibition of ceramidase activity by D-e-MAPP was compared to that by N-oleoylethanolamine, a putative inhibitor of acid ceramidase (Sugita et al, Biochim. Biophys. Acta 398:125 (1975)). N-Oleoylethanolamine was found to be a better inhibitor of acid ceramidase ($IC_{50}$ approximately 500 µM) than D-e-MAPP (FIG. 6C). The effects of N-oleoylethanolamine are consistent with the previously reported $K_i$ of 700 µM (Sugita et al, Biochim. Biophys. Acta 398:125 (1975)). D-e-MAPP demonstrated much greater inhibition of alkaline ceramidase with an $IC_{50}$ of 1–5 µM (FIG. 6C). D-e-MAPP displayed an apparent in vitro $K_i$ for alkaline ceramidase of $2-13 \times 10^6$ µM. At a final concentration of 5 µM, D-e-MAPP inhibited alkaline ceramidase in vitro by approximately 60% whereas N-oleoylethanolamine displayed less than 10% inhibition of alkaline ceramidase in vitro at final concentrations up to 50 µM (FIG. 6D). In contrast, D-e-MAPP was a relatively poor inhibitor of acid ceramidase with less than 10% inhibition of acid ceramidase at 50 μM (FIG. 6C). These results demonstrate that D-e-MAPP is a much superior inhibitor of alkaline ceramides than N-oleoylethanolamine and displays specificity for in vitro inhibition of alkaline ceramidase over acid ceramidase. These results are consistent with the use of 0.5 mM N-oleoylethanolamine to inhibit mitogenesis (Coroneos et al, J. Biol. Chem. 270:23305 (1995)) which is 100-fold higher than the concentration of D-e-MAPP used to inhibit cell growth in FIG. 2.

Figure 7:
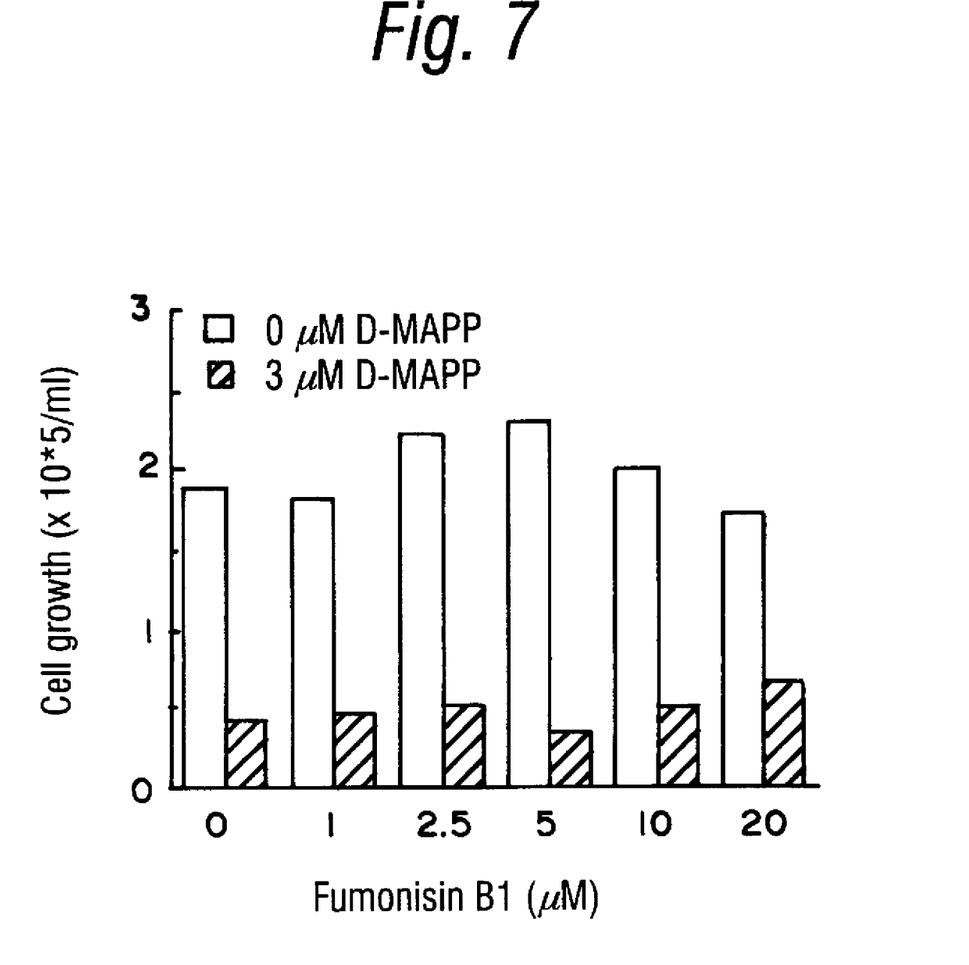
FIG. 7. Effects of fumonisin B1 on growth suppression by D-e-MAPP. HL-60 cells were treated with either vehicle or 3 µM D-MAPP in the presence of the indicated concentrations of fumonisin B1. Cell growth was determined at 48 h.

In addition to ceramidase, inhibition of cerebroside synthase and sphingomyelin synthase or stimulation of sphingomyelinase or cerebrosidase could result in elevations in endogenous ceramide levels. Therefore, the effects of D- and L-e-MAPP were examined on these enzyme activities in vitro and in cells. Neither D- nor L-e-MAPP caused inhibiton of cerebroside synthase activity (Table I). As a control, PMMP, a previously established inhibitor of cerebroside synthase, induced significant inhibition of this enzymatic activity (Table I). Also, D- and L-e-MAPP did not activate or modulate the activity of β-glucosidase. In addition, neither D- nor L-e-MAPP modulated the endogenous levels of sphingomyelin arguing against an effect of either of these molecules on sphingomyelinase or sphingomyelin synthase. In vitro, neither D- nor L-e-MAPP modulated the activity of neutral or acidic sphingomyelinases. Finally, fumonisin B1, an inhibitor of ceramide synthase (45), did not inhibit the effects of D-e-MAPP on growth (FIG. 7).

TABLE I

| Glucosylceramide synthase activity (nmol/h/mg protein) | |
|---|---|
| Control | 1.009 ± 0.0424 |
| D-e-MAPP (20 μM) | 0.946 ± 0.0265 |
| L-e-MAPP (20 μM) | 1.009 ± 0.0383 |
| PMMP (20 μM) | 0.208 ± 0.008 |

Example VI

Effects of D-e-MAPP on Ceramidase Activity in Cells

Figure 8A:
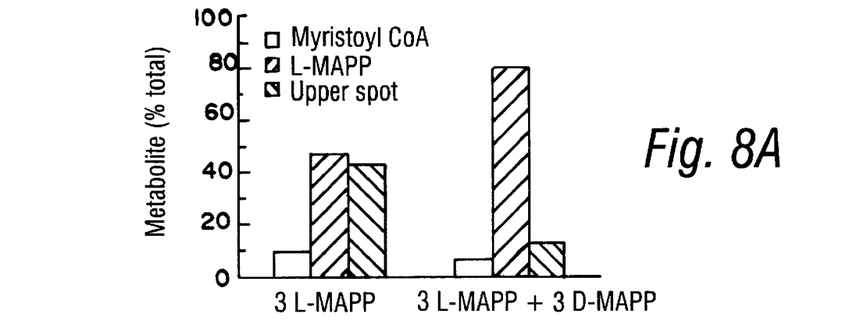
FIG. 8. Interaction of D- and L-e-MAPP in cells. A, the effects of D-e-MAPP on cellular metabolism of L-e-MAPP. HL-60 cells were treated with 3 µM tritium-labeled L-e-MAPP with or without 3 AM D-e-MAPP. Metabolism of L-MAPP was determined. B, concentration dependence of inhibition of L-e-MAPP metabolism in cells. The upper spot on TLC reflects a major metabolite of L-MAPP that probably represents triacylglycerol.
Figure 8B:
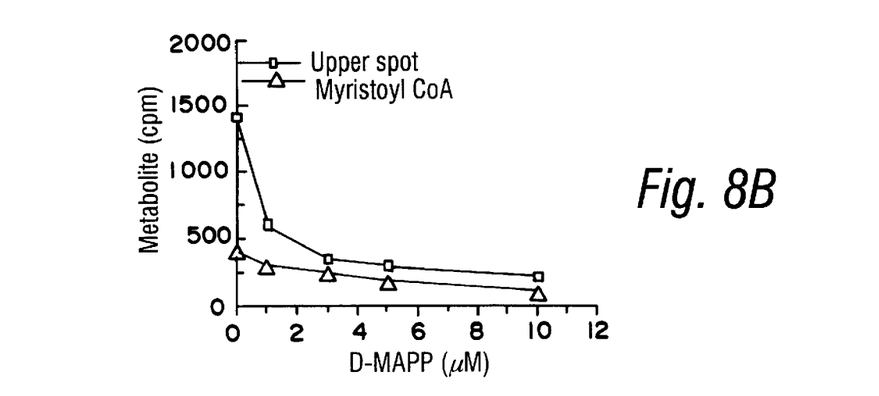
Figure 9:
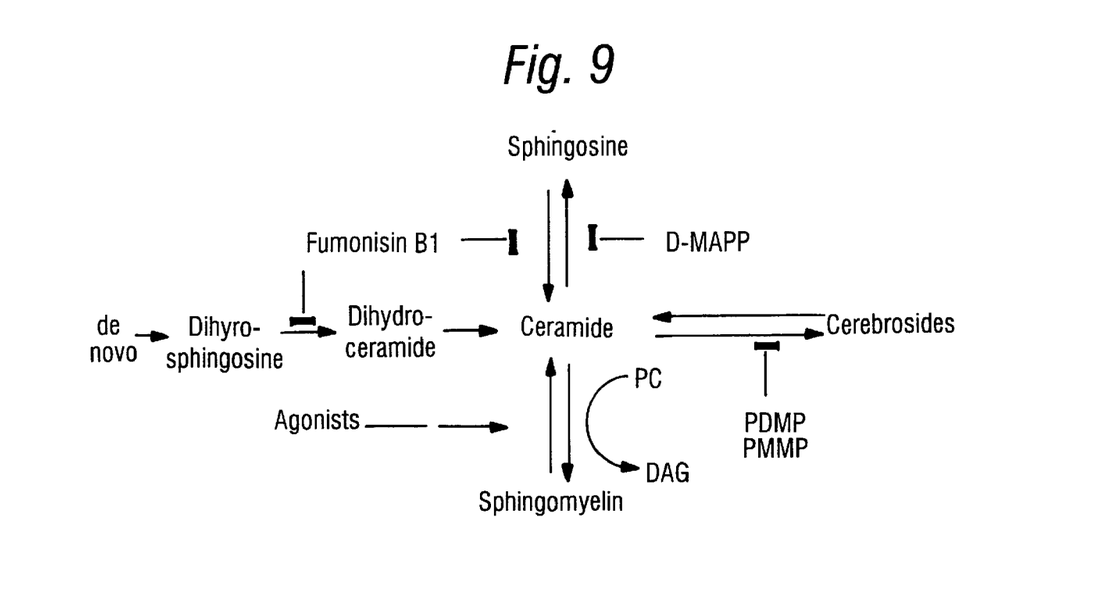
FIG. 9. Scheme of ceramide metabolism and known inhibitors. Ceramide can be interconverted to sphingomyelin, cerebroside, or sphingosine through the action of at least 6 different enzymatic activities: 1) sphingomyelin synthase; 2) sphingomyelinase; 3) cerebroside synthase; 4) cerebrosidase; 5) ceramidase; 6) ceramide synthase.

Since D-e-MAPP inhibits ceramidase in cells, then it should also protect L-e-MAPP from metabolic degradation. Therefore, the effects of D-e-MAPP on metabolism of L-e-MAPP were examined. HL-60 cells were treated with tritium-labeled L-e-MAPP (3 μM), and the metabolism of L-e-MAPP was evaluated in the presence and absence of 3 μM D-e-MAPP. The addition of D-e-MAPP prevented the breakdown of L-e-MAPP (FIG. 8A). The effects of D-e-MAPP on metabolism of L-e-MAPP were dose dependent with most of the inhibition occurring at levels of D-e-MAPP of 1–3 μM (FIG. 8B). Therefore, these studies demonstrate that D-e-MAPP inhibits the metabolism of L-e-MAPP in cells through inhibition of the involved ceramidase.

All documents cited above are hereby incorporated in their entirety by reference.

One skilled in the art will appreciate from a reading of this disclosure that various changes in form and detail can be made without departing from the true scope of the invention.

What is claimed is:

1. A method of increasing intracellular levels of ceramide in a mammal comprising administering to said mammal an agent that inhibits alkaline ceramidase in an amount sufficient to effect said inhibition, and monitoring said intracellular levels of ceramide.

2. The method according to claim 1 wherein agent is a N-acyl-phenylaminoalcohol.

3. The method according to claim 2 wherein agent is D-erythro-2-(N-myristolyamino)-1-phenyl-1-propanol (D-e-MAPP).

4. A method of treating a disease or disorder associated with cell hyperplasia or dedifferentiation comprising administering to a mammal in need of such treatment an agent that inhibits alkaline ceramidase in an amount sufficient to effect said inhibition, and monitoring intracellular levels of ceramide in said mammal.

5. The method according to claim 4 wherein agent is a N-acyl-phenylaminoalcohol.

6. The method according to claim 4 wherein agent is D-erythro-2-(N-myristolyamino)-1-phenyl-1-propanol (D-e-MAPP).

* * * * *